US009234839B2

(12) United States Patent
Hruska et al.

(10) Patent No.: US 9,234,839 B2
(45) Date of Patent: Jan. 12, 2016

(54) PORTABLE SPECTROMETER

(71) Applicant: JDS Uniphase Corporation, Milpitas, CA (US)

(72) Inventors: Curtis R. Hruska, Cloverdale, CA (US); Charles A. Hulse, Sebastopol, CA (US); Brett J. Bryars, Santa Rosa, CA (US); Marc K. Von Gunten, Santa Rosa, CA (US); Christopher G. Pederson, Santa Rosa, CA (US); Nada A. O'Brien, Santa Rosa, CA (US); Jerry Zieba, Santa Rosa, CA (US)

(73) Assignee: Viavi Solutions Inc., Milpitas, CA (US)

( * ) Notice: Subject to any disclaimer, the term of this patent is extended or adjusted under 35 U.S.C. 154(b) by 62 days.

(21) Appl. No.: 14/079,280

(22) Filed: Nov. 13, 2013

(65) Prior Publication Data

US 2014/0131578 A1 May 15, 2014

Related U.S. Application Data

(60) Provisional application No. 61/725,923, filed on Nov. 3, 2012, provisional application No. 61/784,811, filed on Mar. 14, 2013.

(51) Int. Cl.
*G01J 3/42* (2006.01)
*G01N 21/359* (2014.01)
*G01J 5/08* (2006.01)

(52) U.S. Cl.
CPC .............. *G01N 21/359* (2013.01); *G01J 3/42* (2013.01); *G01J 5/08* (2013.01); *G01N 2201/0221* (2013.01)

(58) Field of Classification Search
CPC ...................................... G01J 3/42; G01J 5/08
See application file for complete search history.

(56) References Cited

U.S. PATENT DOCUMENTS

| 4,195,932 | A   |   | 4/1980  | Popelka ........................ 402/13 |
|-----------|-----|---|---------|---------------------------------------|
| 4,382,656 | A   | * | 5/1983  | Gilby ............................ 385/146 |
| 5,347,475 | A   | * | 9/1994  | Taylor et al. ................... 703/12 |
| 5,675,411 | A   |   | 10/1997 | Brooks et al. ................. 356/328 |
| 6,373,574 | B1  |   | 4/2002  | Gu et al. ....................... 356/419 |

(Continued)

FOREIGN PATENT DOCUMENTS

| CA | 2312529 A1 * | 1/2001 |
| EP | 0422448 B1 | 11/1995 |
| WO | WO 2012080478 A1 * | 6/2012 |

OTHER PUBLICATIONS

International Search Report from corresponding PCT application No. PCT/US2013/069910, mailed Apr. 4, 2014.

*Primary Examiner* — Christine Sung
(74) *Attorney, Agent, or Firm* — Harrity & Harrity, LLP

(57) ABSTRACT

A portable spectrometer device includes an illumination source for directing at a sample, and a tapered light pipe (TLP) for capturing light interacting with the sample at a first focal ratio and for delivering the light at a second focal ratio lower than the first focal ratio. A linearly variable filter (LVF) separates the captured light into a spectrum of constituent wavelength signals; and a detector array, including a plurality of pixels, each of the plurality of pixels disposed to receive at least a portion of a plurality of the constituent wavelength signals provides a power reading for each constituent wavelength. Preferably, the TLP is lensed at one end, and recessed in a protective boot with stepped inner walls. The gap between the TLP and LVF is minimized to further enhance resolution and robustness.

21 Claims, 19 Drawing Sheets

(56) References Cited

U.S. PATENT DOCUMENTS

| | | | |
|---|---|---|---|
| 6,420,708 B2 | 7/2002 | Wilks, Jr. et al. | 250/339.07 |
| 6,473,165 B1 | 10/2002 | Coombs et al. | 356/71 |
| 7,006,204 B2 | 2/2006 | Coombs et al. | 356/71 |
| 7,033,056 B2 | 4/2006 | Andersen et al. | 362/554 |
| 7,184,133 B2 | 2/2007 | Coombs et al. | 356/71 |
| 7,218,395 B2 | 5/2007 | Kaye et al. | 356/301 |
| 7,252,399 B2 | 8/2007 | Ferri et al. | 362/19 |
| 7,839,504 B1* | 11/2010 | Newbury | 356/328 |
| 8,373,857 B2 | 2/2013 | Jung et al. | 356/326 |
| 2005/0007596 A1 | 1/2005 | Wilks, Jr. et al. | 356/436 |
| 2006/0044833 A1 | 3/2006 | Li | 362/616 |
| 2009/0195776 A1* | 8/2009 | Durst et al. | 356/326 |
| 2010/0092083 A1* | 4/2010 | Herloski et al. | 382/168 |
| 2010/0290042 A1* | 11/2010 | Vakhshoori et al. | 356/301 |
| 2011/0281367 A1* | 11/2011 | Walte et al. | 436/93 |
| 2012/0056093 A1* | 3/2012 | Poteet et al. | 250/362 |
| 2012/0188541 A1 | 7/2012 | Demmer et al. | 356/326 |
| 2014/0085623 A1* | 3/2014 | Lorbeer et al. | 356/51 |

* cited by examiner

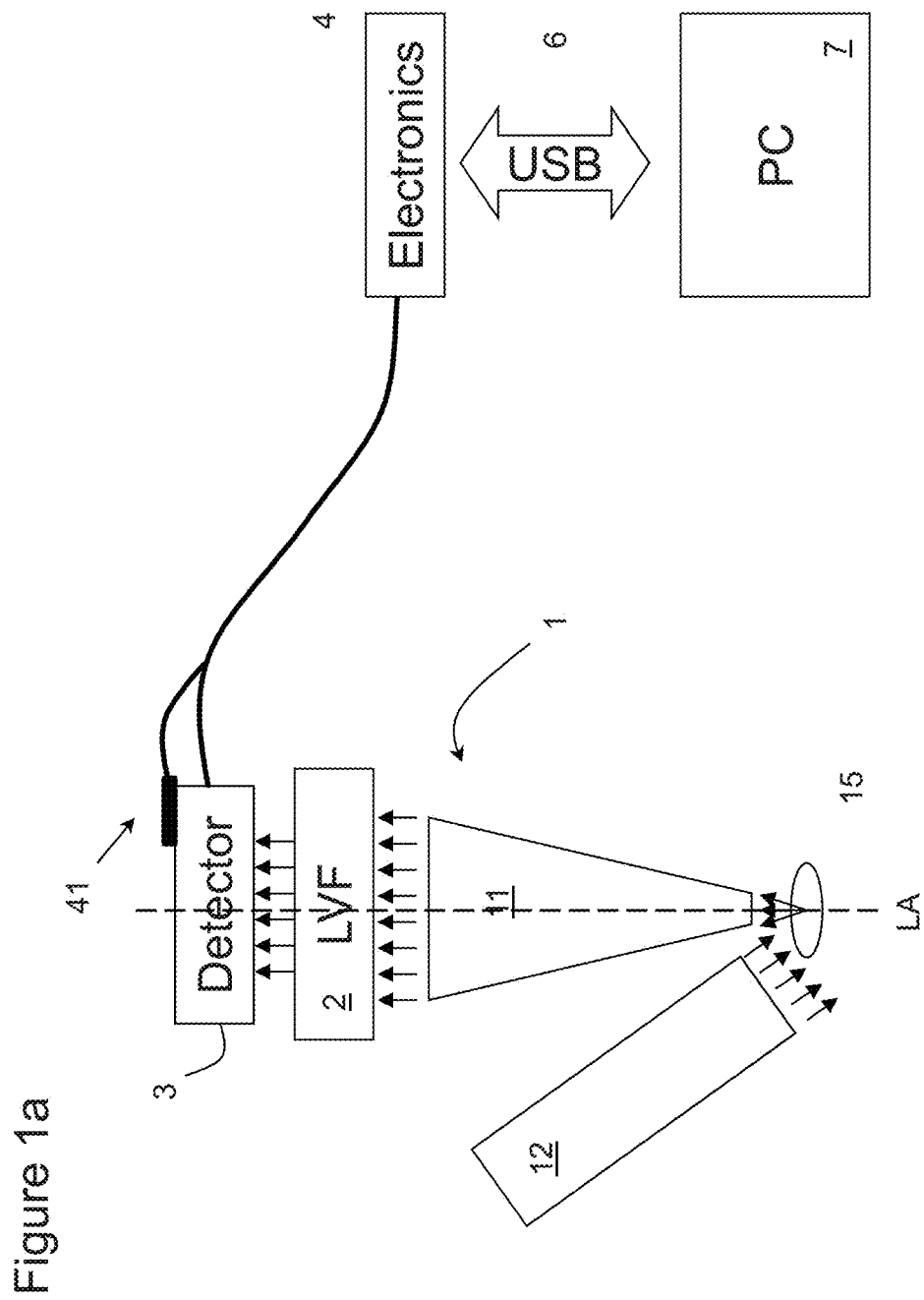

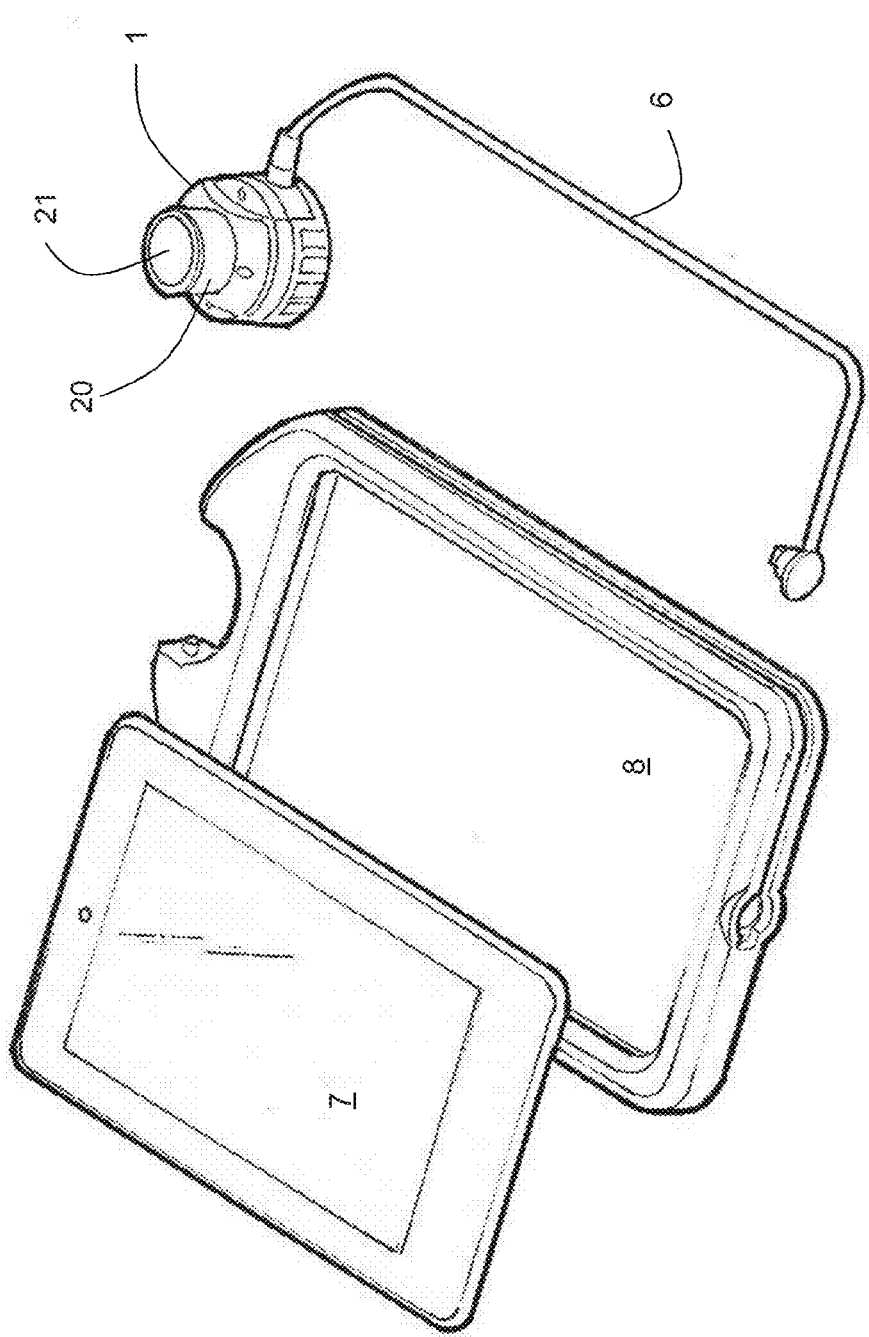

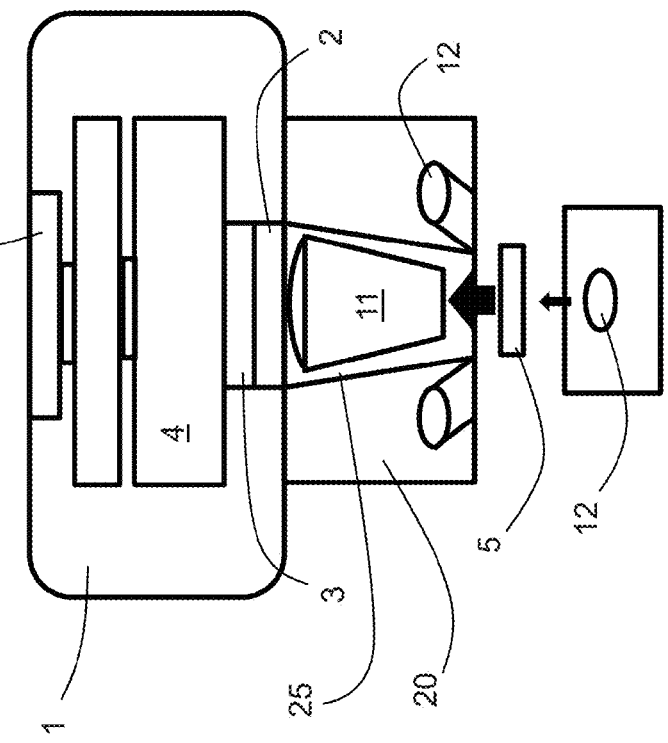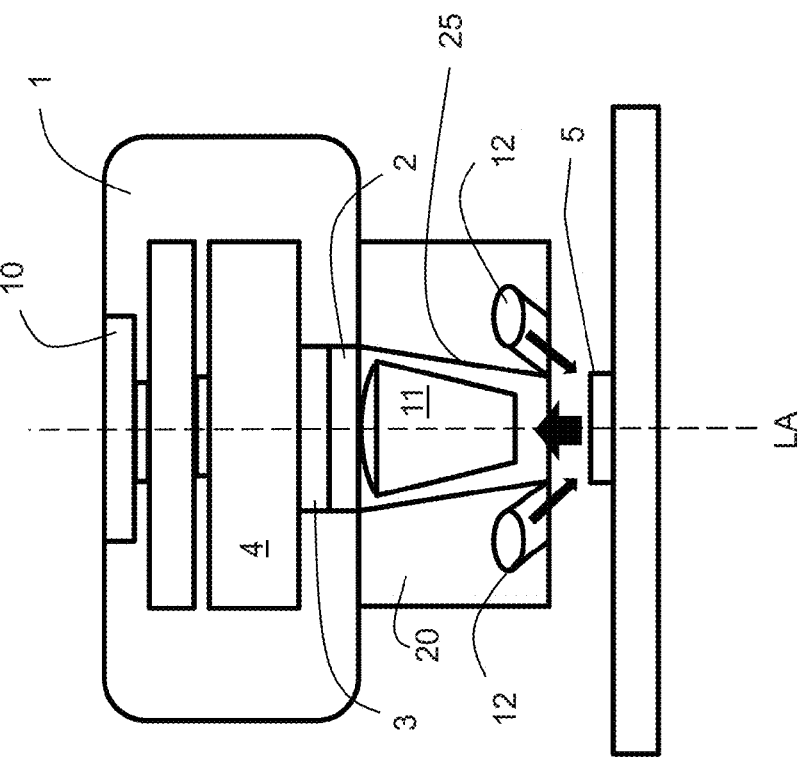

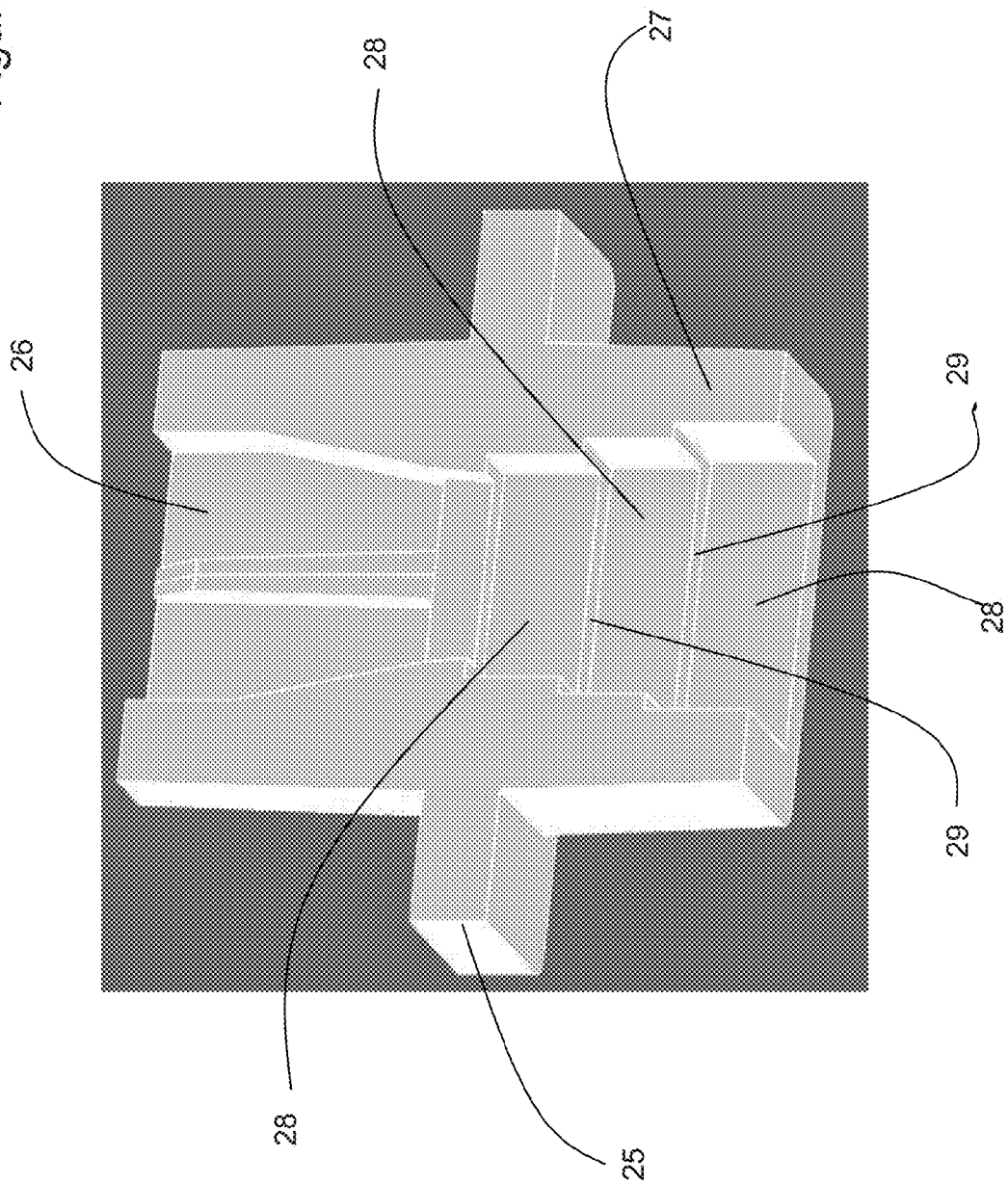

1.7% BW 2.8% BW

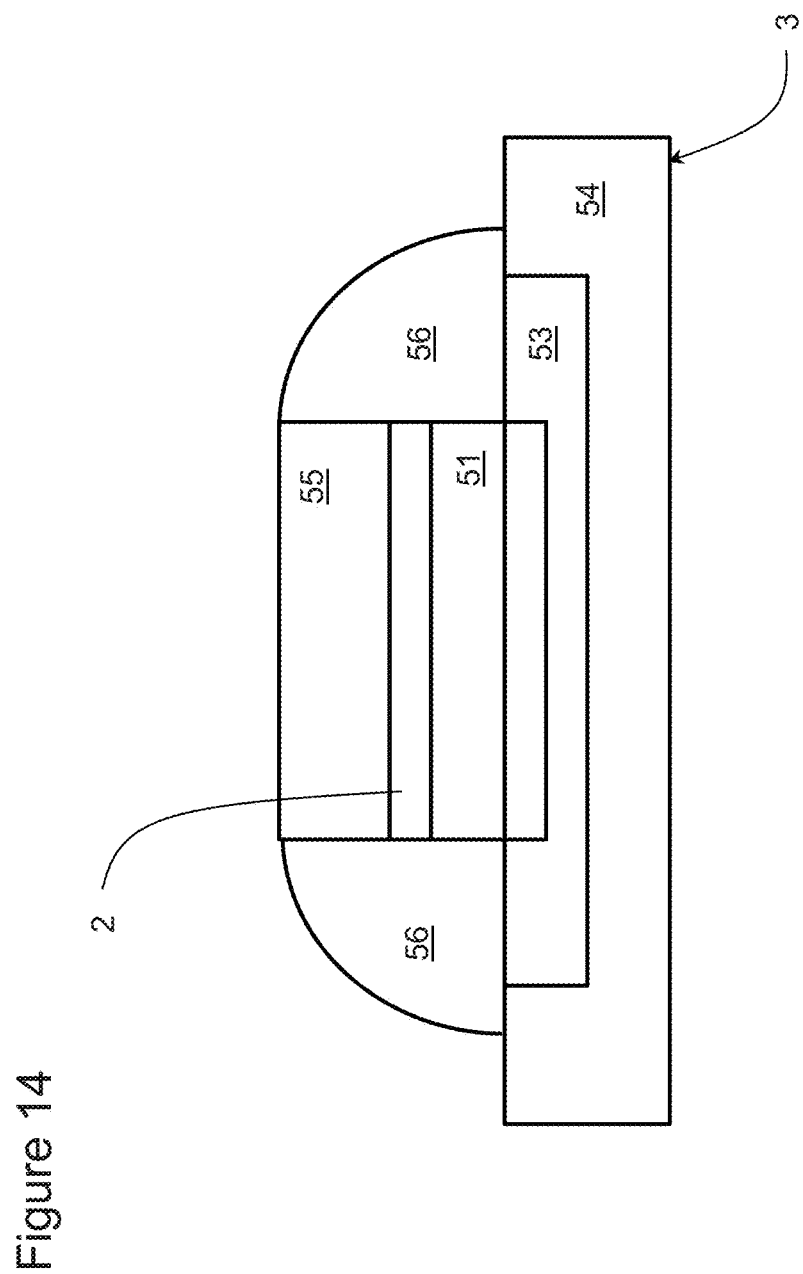

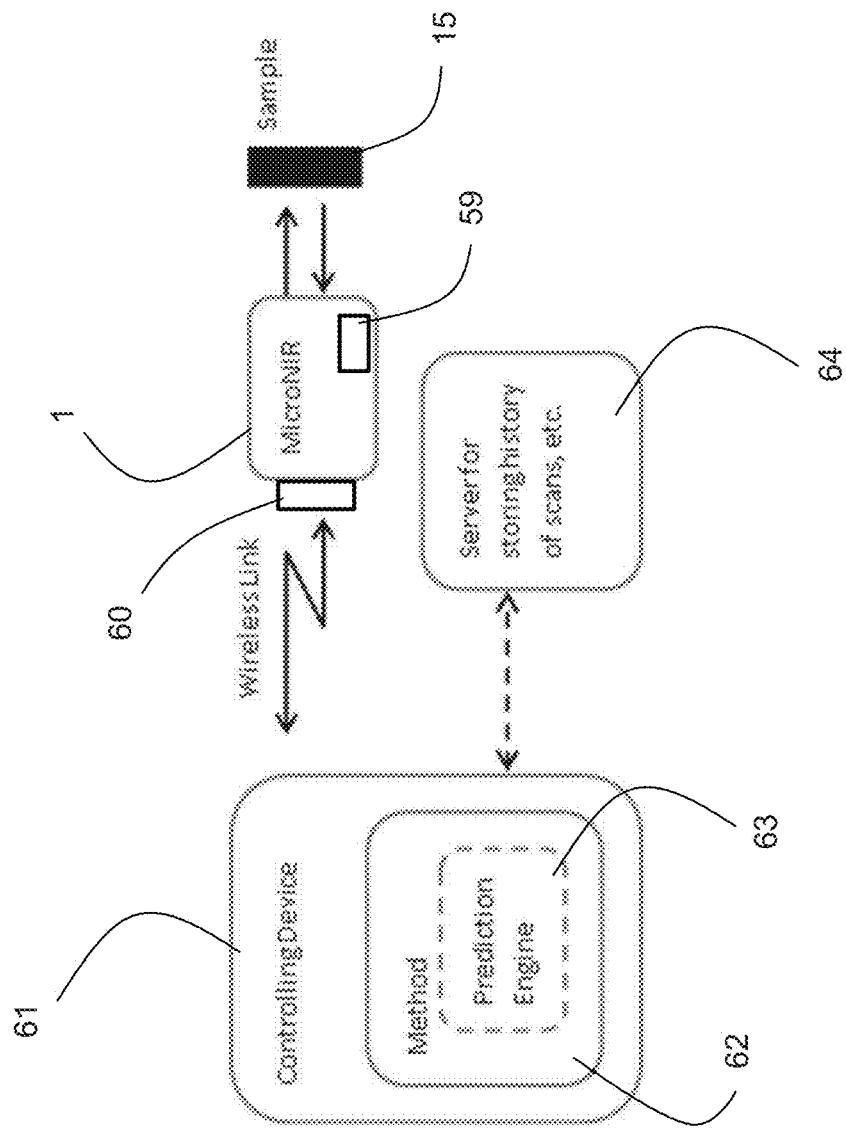

ial Patent Application Nos. 61/725,923, filed Nov. 13,

PORTABLE SPECTROMETER

CROSS-REFERENCE TO RELATED APPLICATIONS

The present invention claims priority from U.S. Provisional Patent Application Nos. 61/725,923, filed Nov. 13, 2012 and 61/784,811, filed Mar. 14, 2013, which are incorporated herein by reference.

TECHNICAL FIELD

The present invention relates to a portable spectrometer, and in particular to a robust, high-performance, portable spectrometer requiring minimal power and size.

BACKGROUND OF THE INVENTION

Over the last decade NIR spectroscopy has increasingly developed to an indispensable analytical tool for production and quality control in the pharmaceutical industry. Qualitative NIR investigations are frequently applied in the identity control of incoming raw materials, whereas quantitative analysis of the final product is an important step in the pharmaceutical process chain. However, the majority of pharmaceutical analyses is still performed by taking a sample from the production site and transporting it to a remote quality control laboratory. This delay between sampling and availability of results limits the frequency of analysis and the optimization of the production line. Thus, novel portable field instrumentation capable of performing a rapid at-line or in-line analysis of the process can be considered as a key tool to advance the effectiveness of the pharmaceutical industry.

Older versions of compact spectrometers, such as the ones disclosed in United States Patent Publication 2012/0188541, published Jul. 26, 2012 to Ocean Optics, Inc, and 2005/0007596, published Jan. 13, 2005 in the name of Wilks Enterprise, Inc. attempt to minimize their footprint by providing a series of optical path folding mirrors. Unfortunately, folding mirrors require extensive alignment procedures during manufacture, and do not provide a very robust structure for field-use devices resulting in low or unpredictable performance.

Historically, light conduits, light pipes or light transfer conduits were used for light beam shaping or light redirection applications. Examples are display engine technologies for displays or front projection television applications, such as those disclosed in U.S. Pat. Nos. 7,252,399 and 7,033,056; and United States Patent Application No. 2006/0044833. U.S. Pat. No. 6,420,708, issued Jul. 16, 2002 to Wilks et al, discloses a spectrum analyzer, which includes a rectangular light pipe or crystal for transmitting light to a sample, but not for shaping the reflected light for delivery to a filter.

U.S. Pat. Nos. 6,473,165; 7,006,204; and 7,184,133 relate to automated verification systems in which the reflectance of two separate beams of light at two different angles of incidence reflected off of an optical interference security feature are measured and compared. A converging tapered light pipe is disclosed for collecting and concentrating light.

An object of the present invention is to overcome the shortcomings of the prior art by providing a high-performance, robust, portable, low-power spectrometer including a broadband light source and detector array for use in an in-the-field sample testing device.

SUMMARY OF THE INVENTION

Accordingly, the present invention relates to a portable spectrometer device comprising:

an illumination source for directing light at a sample;

a tapered light pipe (TLP) for capturing light interacted with the sample at a first focal ratio and for delivering the light at a second focal ratio lower than the first focal ratio;

a linearly variable filter (LVF) for separating the captured light into a spectrum of constituent wavelength signals; and a detector array, including a plurality of pixels, each of the plurality of pixels disposed to receive at least a portion of one of the constituent wavelength signals providing a power reading for each constituent wavelength;

wherein the TLP includes a first smaller end for positioning adjacent to the sample, a second wider and taller end adjacent to the LVF, and sidewalls diverging from the first end to the second end for mixing and spreading the light across the LVF.

BRIEF DESCRIPTION OF THE DRAWINGS

The invention will be described in greater detail with reference to the accompanying drawings which represent preferred embodiments thereof, wherein:

FIG. 1a is a schematic diagram of the spectrometer system in accordance with the present invention;

FIG. 1c is a perspective view of the spectrometer system of FIG. 1a;

FIGS. 2a and 2b are side views of two different embodiments of the portable spectrometer of FIG. 1a;

FIG. 3 is a top view of one of the light sources of the portable spectrometer of FIG. 1a;

FIG. 4 is a top view of a housing of the portable spectrometer of FIG 1a;

FIGS. 5a, 5b and 5c are isometric, side and top views, respectively, of the tapered light pipe of the spectrometer of FIG. 1a;

FIG. 9 is an isometric view of a TLP boot of the portable spectrometer of FIG. 1a;

FIG. 11 is a side view of the LVF of the portable spectrometer of FIG. 1a;

FIG. 12 is a schematic view of the LVF and detector array of the portable spectrometer of FIG. 1a;

FIG. 14 illustrates a side view of a LVF and detector array structure in accordance with the present invention;

FIG. 15 is a schematic illustration of a wireless spectrometer system in accordance with the present invention.

DETAILED DESCRIPTION

Figure 1B:
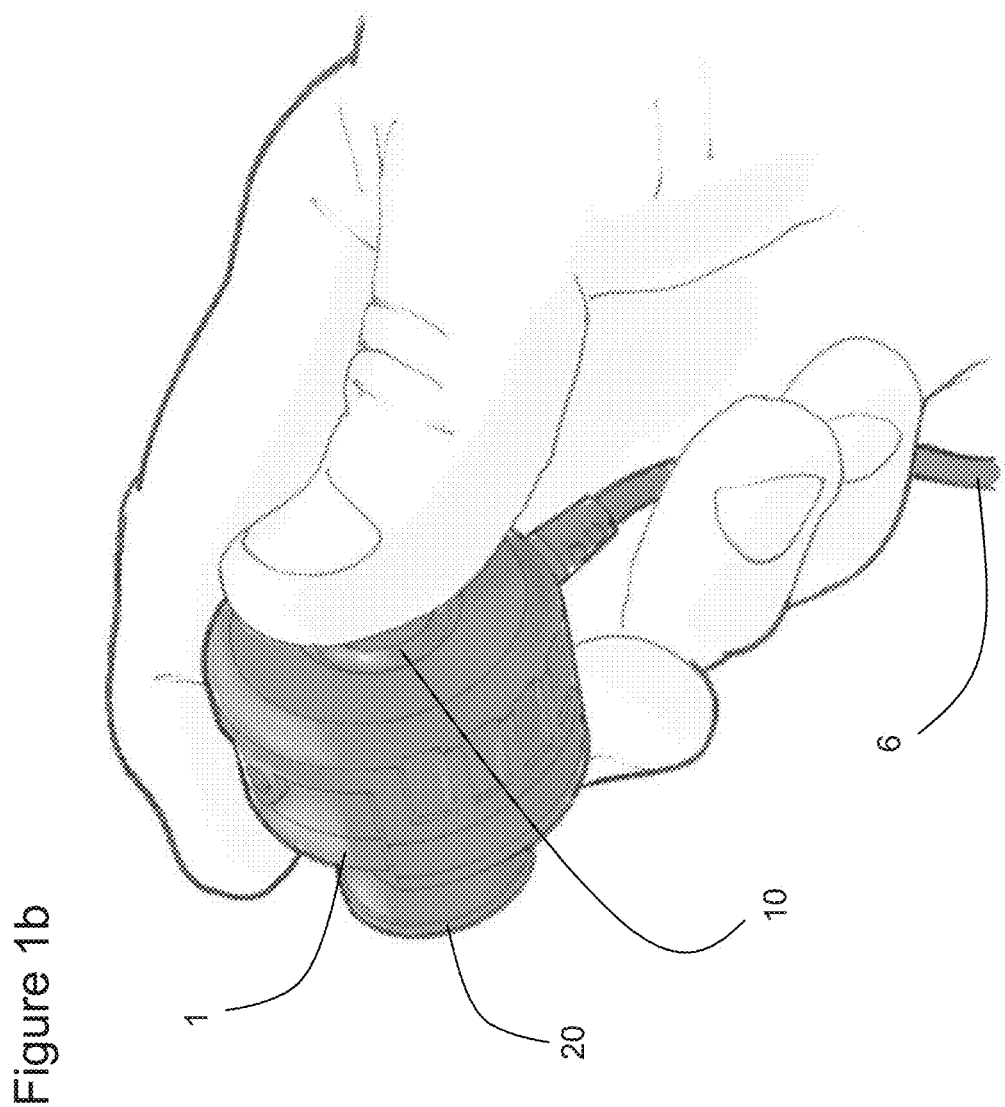
FIG. 1b is a perspective view of the spectrometer of FIG. 1a in a user's hand.
Figure 3:
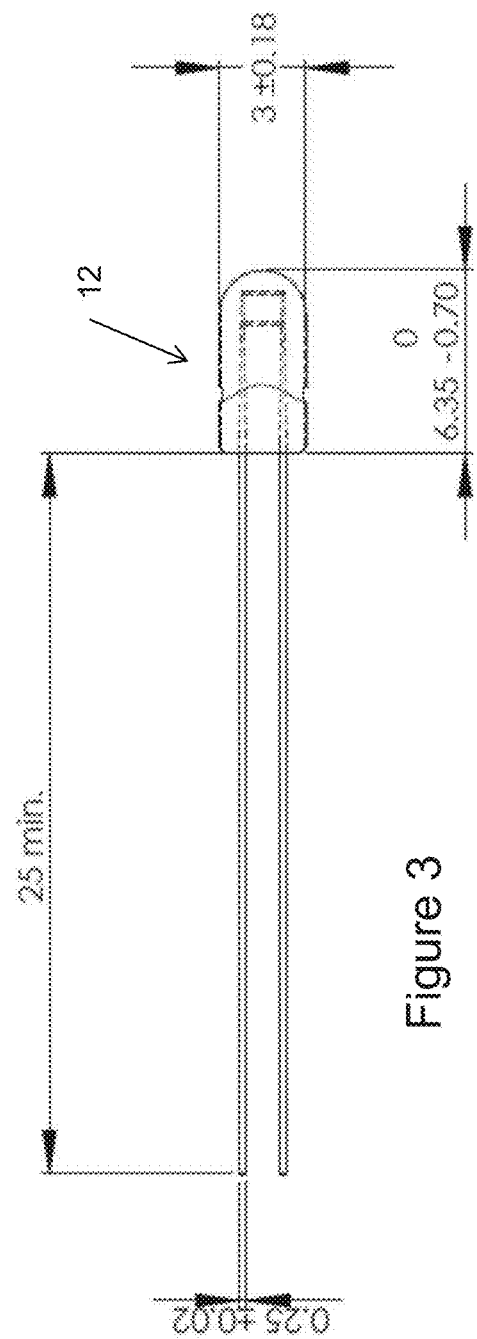

With reference to FIGS. 1a, 1b, 1c, 2a and 2b, a compact spectrometer 1, in accordance with the present invention, is a very small, e.g. less than 5 pounds, preferably less than 2 pounds, more preferably less than 0.5 pounds, and ideally less than 100 g without battery, compact, e.g. less than 6"×6"×2', preferably less than 6"×3"×1", and more preferably less than 4"×2"×0.5", low-cost hand-held spectrometer built around a light filter 2, mounted on a broadband detector array 3, e.g. more than 500 nm, preferably more than 600 nm and most preferably more than 700 nm wide, such as an indium gallium arsenide (InGaAs). The light filter could be any form of spectrometer, e.g. diffraction based, phase holographic, frustrated total reflection (FTR) or linearly variable filter (LVF) based instruments, that requires a specified input cone angle to function, but an LVF is preferred.

The LVF is a dielectric thin-film Fabry-Perot bandpass filter deposited using energetic processes, well known to produce stable and reliable optical components. The filter coating in the LVF is intentionally wedged in one direction. Since the center wavelength of the bandpass filter is a function of the coating thickness, the peak transmitted wavelength varies continuously along the direction of the wedge. The LVF is typically fabricated from inorganic materials, such as $SiO_2$ and $Ta_2O_5$, produced by ion-assisted physical vapor deposition techniques resulting in dense coating with high reliability and stability.

Ideally, the spectrometer 1 is entirely USB-powered, i.e. the spectrometer is powered by 2.5 W or less, but battery power with a wireless connection is within the scope of the invention, as will be detailed hereinafter. A control system 4, comprised of a processor and suitable non-transitory memory, includes a suitable USB connector for receiving a USB cord 6, enabling the transfer of data between the control system 4 and a host controller device 7, e.g. laptop, notebook, notepad or pda, ideally housed in a protective cover 8. One or more self-contained light sources 12 activated by switch 10 are used to direct light onto a sample 15 so that the diffusely reflected, transmitted or otherwise interacting radiation will be captured by a light collection optic, e.g. a tapered light pipe (TLP) 11, for delivery to the light filter, e.g. LVF 2.

In order to minimize the size of the spectrometer 1 and the operating power consumption, while maintaining robustness and high performance many problems had to be solved including: 1) making the light path as efficient as possible; 2) using the TLP 11 in the train instead of fibers, 3) placing the LVF 2 close to the detector 3 to minimize the optics required; 4) leaving the detector array 3 uncooled, to avoid the power requirement of a TE cooler; and 5) providing light source(s) 12 that consume as little power as possible, but still provide broadband illumination, e.g. in the IR region.

The spectrometer 1, in accordance with the present invention, consumes less than 2.5 W of power when operating, even when the light sources 12 are comprised of two or more lamps. For near infrared, the light sources 12 are preferably comprised of one or two onboard incandescent lamps, e.g. vacuum tungsten lamps, that provide broadband illumination, e.g. over 500 nm, preferably over 700 nm, most preferably over 1000 nm across the active range of the instrument, e.g. for the NIR in the 900 nm to 1700 nm range or in the 900 nm to 2150 nm range. One lamp 12 is sufficient; however, two lamps 12 adds more light for the sample to interact with, hence shorter integration times. There is a practical limit; however, space constraints and USB or battery power limits.

Figure 4:
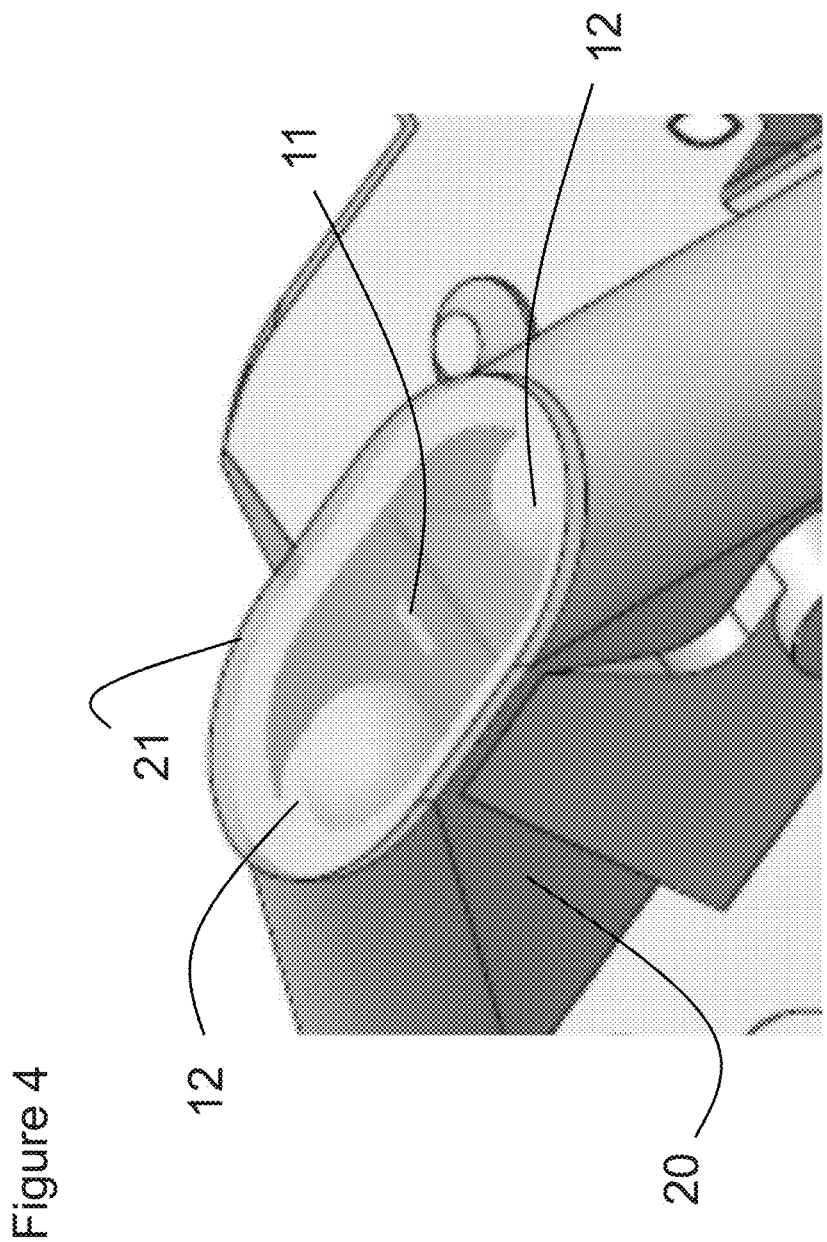

With reference to FIGS. 2a and 2b, there are typically two configurations for the light sources 12. In one configuration, the sample 15 is illuminated at an acute angle from normal to the sample 15, e.g. 45° from a longitudinal axis LA of the TLP 11, with relatively collimated light from one, two or a plurality of light sources 12, and with an end of the TLP 11 disposed equidistant between each lamp. The longitudinal axis LA of the TLP 11 is perpendicular to the substrate of the LVF 2 and the detector array 3. In the other arrangement, the sample 15 is flood illuminated. In both arrangements, the receiving end of the TLP 11 is disposed to receive light at substantially normal incidence from the sample 15, i.e. along the longitudinal axis LA. The light sources 12 are disposed to exclude specular reflection from the sample 15. The 45° illumination diffuses reflectance or transflectance measurements. Each light source 12, ideally comprises a lens tipped vacuum tungsten lamp for creating a 5 mm, preferably 3 mm or less, spot on the sample 15. With reference to FIG. 4, the light sources 12 and the end of the TLP 11 are ideally recessed in a housing 20, which extends outwardly from a main body of the device 1. The housing 20 has an opening covered by a transparent, e.g. sapphire, protective window 21 through which the light is projected onto the sample 15, and the reflected light is captured by the TLP 11. The housing 20 protects the light sources 12 from damage, and prevents stray light from external sources from entering the end of the TLP 11. Both reflectance and transmission modes, in which the sample 15 is placed between the light source 12 and the TLP 11, are possible, as illustrated in FIGS. 2a and 2b, respectively.

The concept of a small portable body, also could include, but not limited to, a small screen on the back for viewing spectra, a simple point-and-shoot interface, a battery, a memory card for storing spectra, a computer interface, a flash or onboard illumination source, and a framework for building, loading and using onboard "applications" for post-processing the data.

The first embodiment of the light sources 12 incorporated the use of two lens tipped vacuum tungsten lamps to present intense NIR light to the sample 15. Ideally, the lamps are orientated so that light would strike the sample 15 at an acute angle, e.g. 45°, from normal to the sample, and specular reflections would reflect into the opposite lamp. Ideally a 3 mm diameter spot is created on the sample 15. No direct specular reflection would, under normal conditions, enter into the entrance aperture of the TLP 11. This is still a viable illumination condition, but has one drawback, i.e. the two projected beams coincide at one location with a "measurement depth of field" of ~500 μm. Many, if not most, NIR measurements measure light from the surface as well as within the sample, i.e. penetrating depth can be as great as 10 mm in some cases. This illumination, while excellent for controlling specular reflection, can create variable transflectance results. If the sample 15 is being measured at its surface only this is a viable illumination arrangement.

The light sources 12 of the alternative embodiment incorporates flood illumination with non-directional lamps. The flood illumination bathes the sample 15 with non-collimated light that mitigates the "measurement depth of field" problem, i.e. up to 10 mm for transflectance measurements, not just surface measurements. Flood illumination is also able to deliver more NIR light flux to the sample 15 being measured. The extra degrees of freedom come at a price of needing to control parasitic specular light from the front protecting window 21 of the spectrometer 1. This is achieved with the use of a terraced boot 25 (See FIG. 7) that strictly defines the field of view as seen by the entrance aperture of the TLP 11. Mitigation of unwanted light from the lamps 12 into the TLP 11 is achieved by position of the lamps 12 with respect to the entrance aperture of the boot 25, how close the boot 25 is from the rear surface of the window 21, how thick the window 21 is and coatings applied to the window 21 to minimize specular reflection.

The TLP 11 provides light collection optics designed to present spectral light energy at any desired wavelength, i.e.

reflected from a lambertian scattering surface or transmitted translucent surface of the sample 15, to the input surface of the LVF 2 for transmission to detector array 3. In order for the filter/detector array assembly ⅔ to operate efficiently, light entering the LVF 2 needs to have maximum acceptance NA of 0.2 or smaller. To achieve an acceptable NA the output radiation pattern collected from the sample 15 being measured requires a lens or a tapered light pipe. The tapered light pipe 11 can be solid, e.g. Schott N-BK7 glass, or hollow in construction, depending on the spectral engines or spectrometers operating parameters. The taper angle of the TLP 11 can be optimized for reflection or transmittance type sampling and/or optical path length. The TLP 11 can have a reflective coating applied for either the hollow or solid designs or without coatings. Tapered and non-tapered light pipes may or may not have light recirculation properties to increase signal from the sample. Spectrometer or spectral sensory will dictate the wavelength region of interest and ultimately govern light pipe design.

Figure 5A:
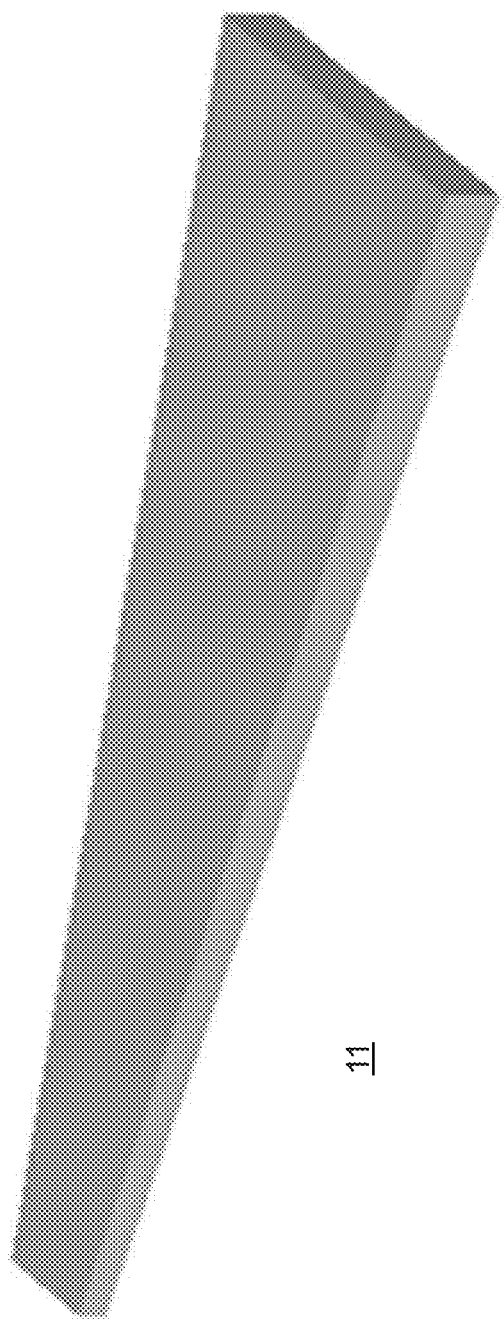
Figure 5B:
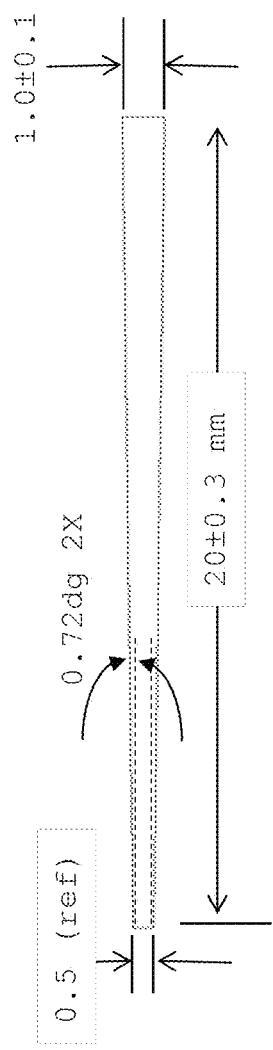
Figure 5C:
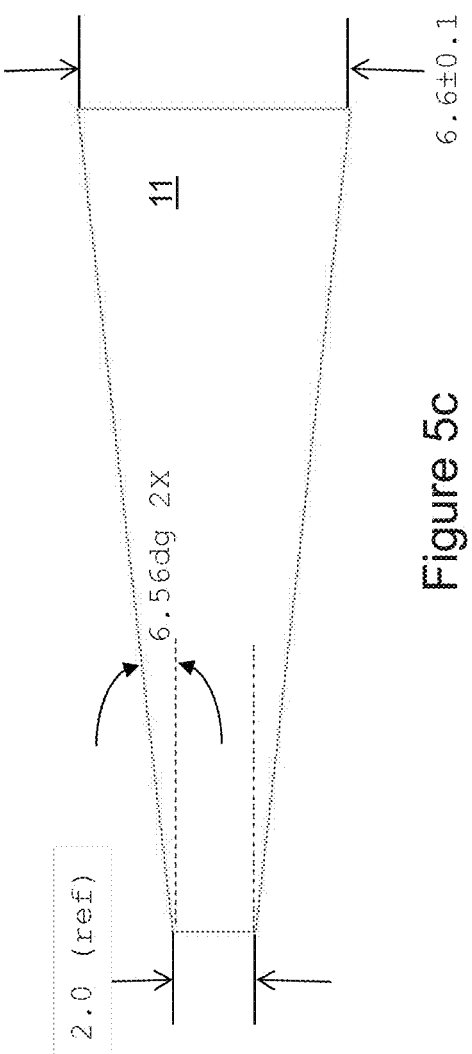

The tapered light pipe (TLP) 11, a specific example of which is illustrated in FIGS. 5a, 5b and 5c, captures light at a first smaller end from lambertian light sources, i.e. reflections of the lamps 12 from a highly scattering surface, e.g. solid or liquid samples 15, at a first focal ratio, e.g. f/1, and cone angle, e.g. between 20° and 40°, but typically about 30°, and mixes, spreads out and reshapes the reflected light into the required lower focal ratio f/3, i.e. cone angle of about 10° or less, required for better operation by the LVF 2 within the spectrometer 1. The tapered light pipe 11 acts as a disperser and light reshaping device with diverging sidewalls, e.g. four, that spreads out the light and enables the electromagnetic waves to pass from a second larger end, e.g. taller and wider, through the LVF 2 from the lambertian illuminated surface. Accordingly, the TLP 11 enables the spectrometer 1 to sample light from a relatively large area, collecting light from any lambertian scattering surface, contrary to competing technologies, which generally collect light with fiber optic that originates from a small localized area. Moreover, the TLP 11 mixes and spreads out the light to accommodate the size of the LVF 2 and the pixels in the pixel array 3. The LVF 2 can then be optimized to accept light that deviates less than 10° from a normal, i.e. to the coating surface and/or the LVF substrate, thereby greatly improving resolution and performance.

The focal ratio is the ratio of the focal length of the telescope to its aperture. It's calculated by dividing the focal length by the aperture. For example, a telescope with a 2032 mm focal length and an aperture of 8" (203.2 mm) has a focal ratio of 10 (2032/203.2=10) or f/10.

Figure 6:
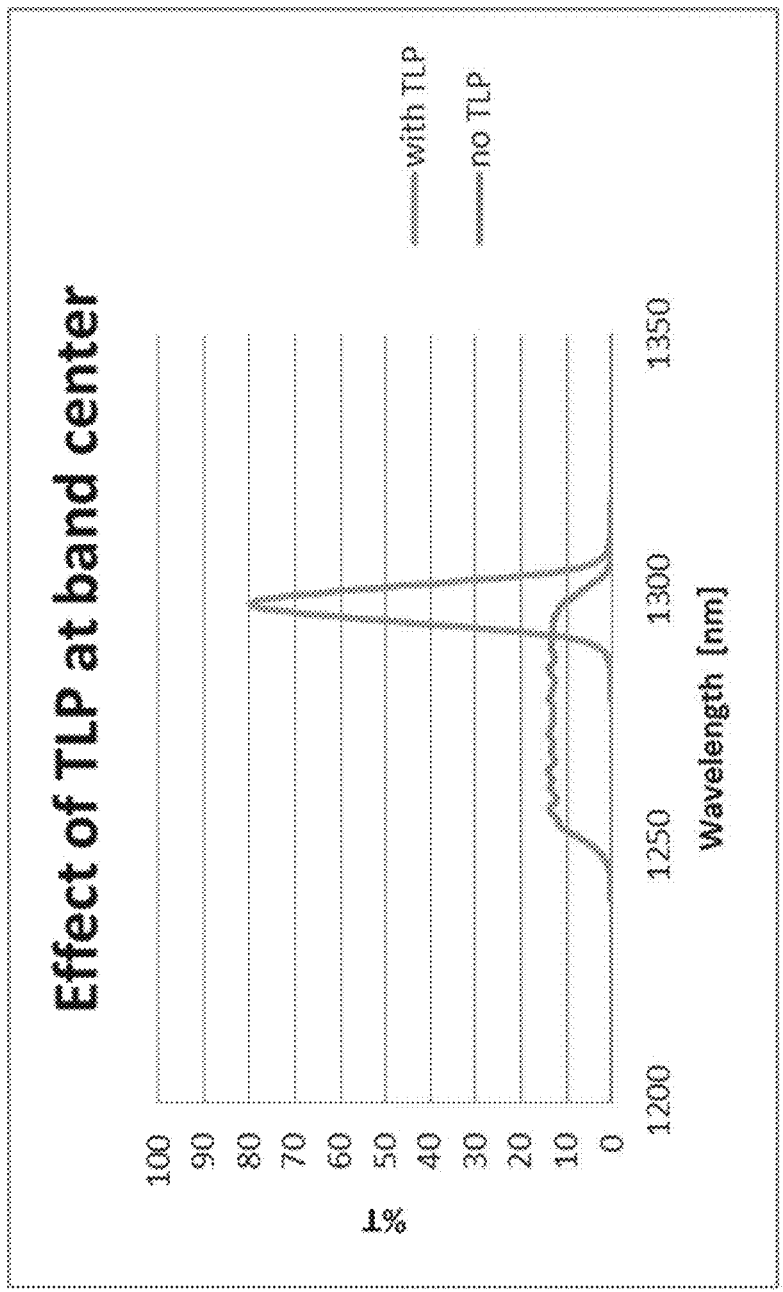
FIG. 6 is a plot of transmission vs wavelength for a spectrometer with and without a TLP.

The TLP 11 is a light beam steering/reshaping device that employs compound angles to slow an optical light cone from a first (fast) focal ratio, e.g. f/1, to a second lower (slower) focal ratio, e.g. f/3, and enable the LVF 2 to spectrally perform. This is accomplished by controlling the aspect ratio of the entrance and exit apertures of the TLP 11. The length of the TLP 11 needs to be long enough to achieve sufficient mixing of the light and achieve the proper (slower) focal ratio at the exit aperture. FIG. 6 illustrates the difference in transmission, i.e. much less, and wavelength, i.e. much broader, for a spectrometer with or without the TLP 11.

The entrance aperture of the TLP 11, closest to the lamps 12, has a smaller opening of 1.5 to 2.5 mm (preferably 2 mm +/−0.1 mm)×0.4 mm to 0.6 mm (preferably 0.5 mm +/−0.1 mm. The exit aperture, proximate the LVF 2, has a larger opening 6 to 7 mm (preferably 6.6±0.1 mm) wide and 0.75 to 1.25 mm (preferably 1.0±0.1 mm) long. The length of TLP 11 is 15 to 25 mm (preferably 20±0.3 mm) tapering in both height and width to the entrance end. Accordingly the taper angle is between 6° and 7° per side from the longitudinal axis, with a total of 12° to 13° for the width, and between 0.5° and 1° per side from the longitudinal axis, with a total of 1° to 2° for the height.

Figure 7A:
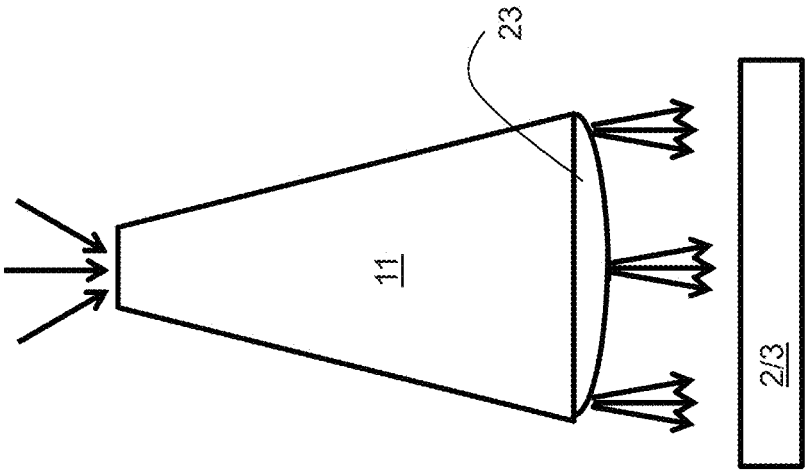
FIGS. 7a and 7b illustrate incoming and outgoing ray bundles from a standard TLP and a lensed TLP, respectively.
Figure 7B:
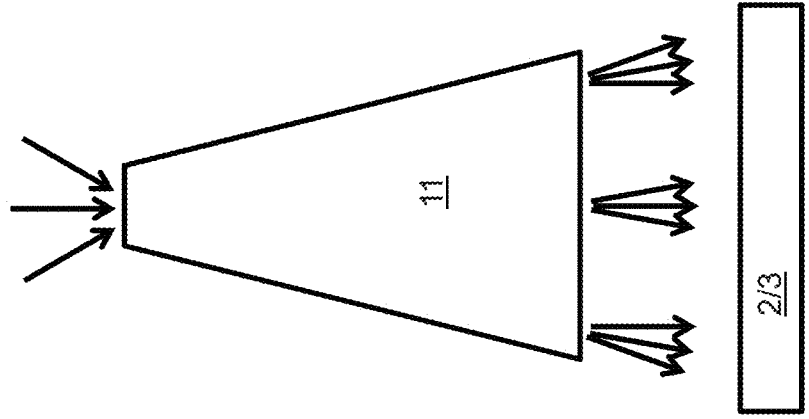
Figure 8:
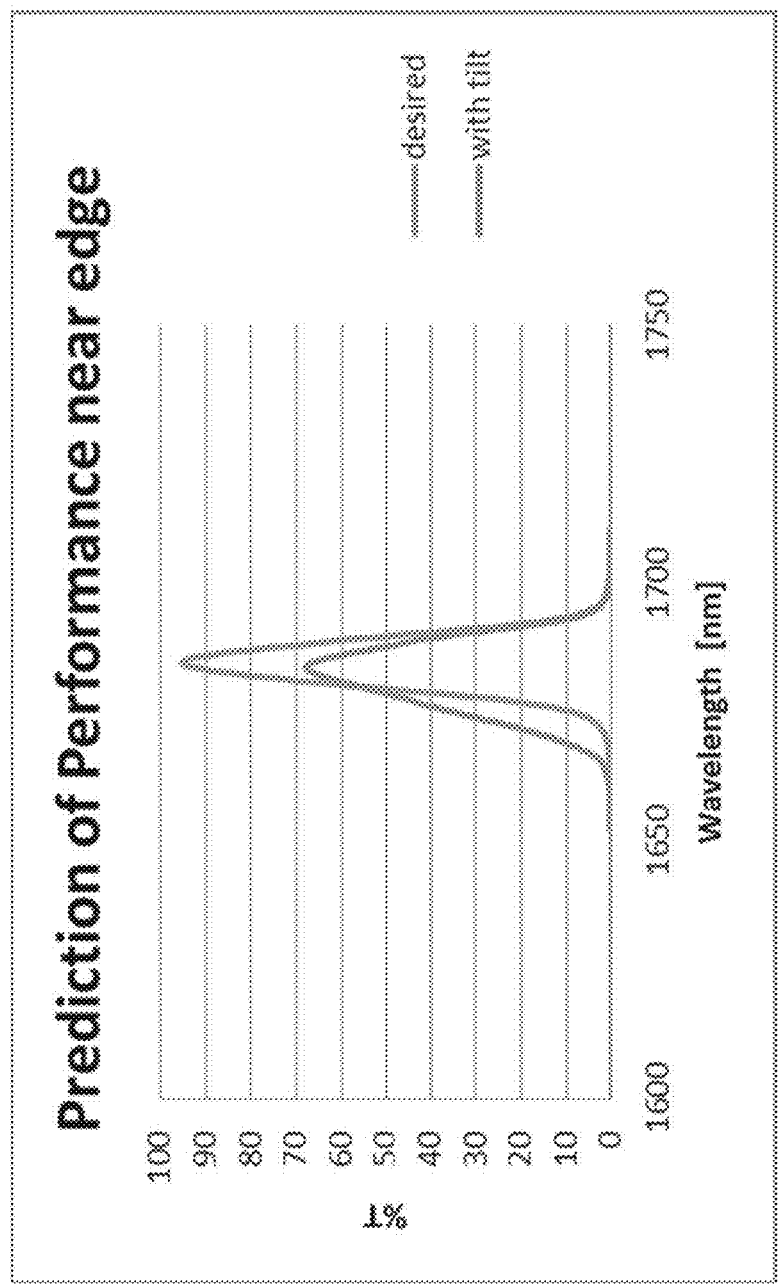
FIG. 8 is a plot of transmission vs wavelength for a spectrometer with and without a lensed TLP.

Unfortunately, as a result of the TLP 11, the ray bundles exiting the TLP 11 are no longer normal to the LVF 2, i.e. they tilt up to 6° on either end of the detector array 3 (See FIG. 7a). As a result two bad effects occur, which are worse at the ends of the detector array 3: 1) there is a downshift in center wavelength; and 2) there is a broadening of the bandwidth (resolution). The shorter, broader plot in FIG. 8 illustrates the performance of a spectrometer with a flat TLP 11.

The introduction of lensed elements in the TLP 11 to straighten tilted ray bundles could be ideally in the form of a lensed face 23 to the TLP 11; however, a separate lens and/or a lensed entrance to the LVF 2, are also possible. With a cylindrical lens 23, e.g. 0.5 mm sag over a 6.4 mm active area, using typical optical material, the tilted rays at the edge of the detector array 3 can be straightened, which should recover optimal performance of the MicroNIR, e.g. linear wavelength spacing and optimal resolution. See the taller and thinner plot in FIG. 8.

With reference to FIG. 9, a TLP boot 25 is provided for supporting the TLP 11, and functions to ensure that the reflected light from the sample 15 is presented to the entrance aperture of the TLP 11 at the proper acceptance angle defined by a first focal ratio, e.g. f/1 with a cone angle of about 30°, and that the field of view for the TLP 11 is delivered to the LVF 2 at the required second focal ratio, e.g. f/3, with a cone angle of about 10°. The boot 25 includes a support section 26, which supports at least the tip of the TLP 11 and ideally all of the TLP 11 without introducing strain, thereby protecting the TLP 11 from shock and vibration. The boot 25 also includes a spacer section 27, which reduces the amount of the lamps 12 specular reflections from the protective window 21 from reaching the entrance aperture of the TLP 11 by recessing the TLP 11 and spacing the entrance end of the TLP 11 from the protective window 21. The spacer section 27 is in direct contact with the entrance aperture of the TLP 11, and includes a plurality of stepped inner surfaces 28, with a plurality of flat rectangular terraces 29 with surfaces extending around the opening and perpendicular to the longitudinal axis LA of the TLP 11, for reducing NIR light energy from entering the TLP 11 at any other location, e.g. reflected from input window. The side walls of the spacer section 27 converge in a step-wise manner in length and width from the opening thereof to the opening of the TLP 11, which is disposed within the boot 25. If light does enter from other sites then the result is poor spectral performance of the system. The terraces 29 are analogous to focus bellows of the old plate cameras, and are very effective at blocking and trapping unwanted scattered light from entering into the TLP 11. For the spectrometer 1, this enables higher OD measurements for transflectance measurements in addition to better utilization of the detectors dynamic range.

Figure 10B:
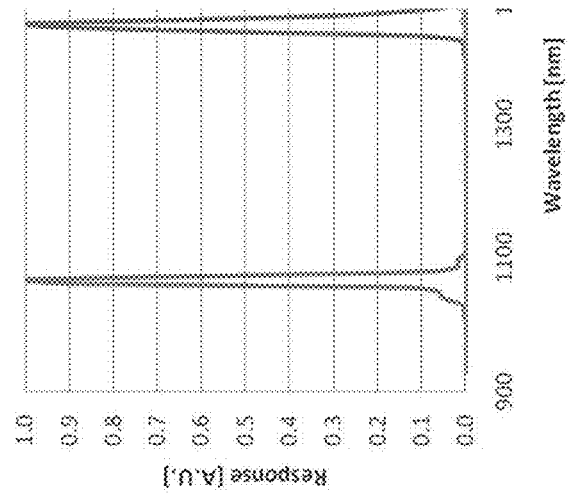
FIGS. 10a and 10b are plots of response vs wavelength for a spectrometer with and without the TLP boot, respectively, of the present invention.
Figure 10A:
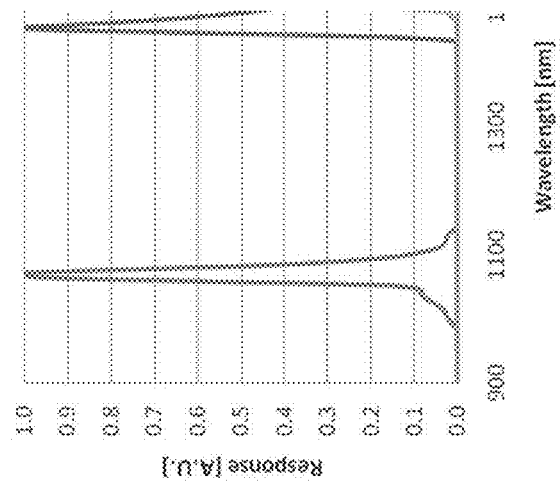

If higher angle light flux enters into TLP 11 at the entrance aperture the result is broadening of the spectral bandpass, secondary spectral peaks, shoulders and pedestals on the spectral profile. The plots in FIGS. 10a and 10b illustrate the difference in a laser line spectral profiles for a conventional boot (FIG. 10a), and the boot 25 (FIG. 10b) of the present invention, which provides much higher resolution.

Figure 11:
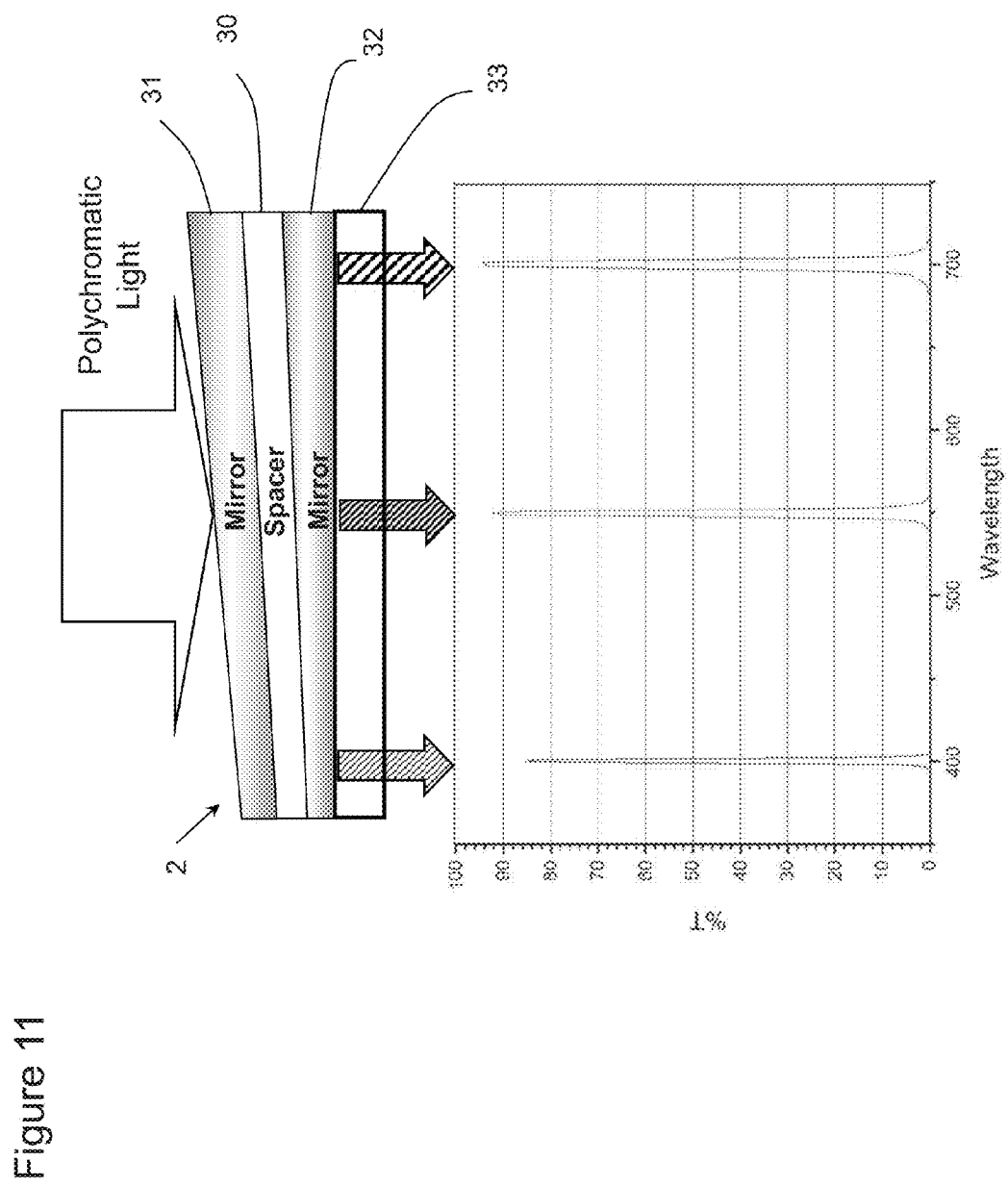
Figure 12:
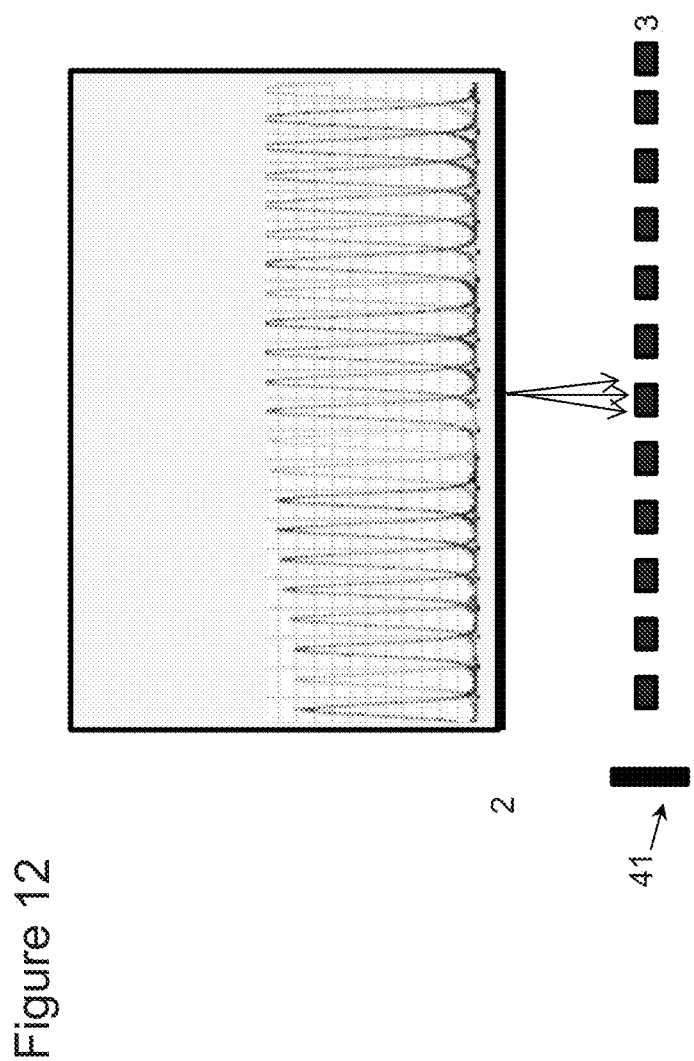

With reference to FIGS. 11 and 12, the LVF 2 of the present invention receives the collected light from the TLP 11 and transmits individual wavelength bands, which vary linearly across the length of the LVF 2 in ascending or descending order. In the illustrated embodiment, the LVF 2 comprises multi-layer stack with a spacer layer 30 between first and second reflector layers 31 and 32 on a substrate 33, as is well known in the art. The first and second reflector layers 31 and 32 are deposited with a tapering (converging or diverging) thickness in cross section, whereby the thicker the filter the longer the transmitted wavelength, The illustrated graph of % transmission vs wavelength includes wavelengths from 400 to 700; however, any range of wavelengths is possible.

The center wavelength varies continuously along the length of the LVF 2, so the light hitting a detector pixel is the superposition of the bandwidths emanating from every point on the LVF 2 that the pixel can "see" (set by the F/# of the light). The center transmission wavelength varies linearly across the length of the LVF 2. In the example the extreme left end of the LVF 2 transmits a narrow range of blue wavelength only (shorter wavelength). As you move to the right the thickness of the LVF 2 increases and a longer wavelength is transmitted. Eventually at the extreme right only a narrow band of red light (longer wavelength) is transmitted.

The LVF 2 is designed to transmit a band of wavelengths at each position. The bands are designed to be comparable to, though usually less than, the total intended wavelength range divided by the number of pixels. For example, in the existing spectrometer 1 with 128 pixels, the LVF 2 is designed to transmit a band of about 1% of the central wavelength (10 nm at a center wavelength of 1000 nm). One of the strengths of LVF technology is that the bands are not separated; in other words, every wavelength hitting the LVF 2 will be "seen" somewhere at the detector plane.

Instead of a power hungry and bulky cooling system, a temperature feedback device 41, e.g. thermistor, is ideally mounted in close proximity to the detector array 3. The temperature-feedback device 41, can be either a thermistor, which changes resistance with temperature, or a precision IC, which outputs a known temperature-dependent voltage. The analog output of the temperature feedback device is read by the control system 4 CPU. The control system 4 can then perform a temperature adjustment process to determine a temperature adjusted reading by accessing a look up table or formula stored in non-volatile memory that corrects the initial measurements based on the temperature from the temperature feedback device.

The dark current and responsivity of the detector array 3 are temperature dependent. Repeatable results are possible as long as the temperature is stable; however, conventional wisdom is that the temperature of the LVF 2 and detector array 3 should be as low as possible.

In all applications, the gap between the LVF 2 and the detector array 3 is set to minimize the spread of the beam of any wavelength emitting from the LVF 2; e.g. to optimize the beam spread to under three pixels on the detector array 3. An alternate embodiment would be to space the gap to ensure that the beam does not double in size between the LVF 2 and the detector array 3.

FIG. 12 illustrates the importance of a small gap d between the LVF 2 and the detector array 3. Assuming the light has the same cone, provided by the TLP 11, as the light hitting the LVF 2, i.e. f/3 or 9.59°, the spread S becomes d×tan 9.59°. For a gap d of 150 um, the spread becomes 25 um. Accordingly, a single line on the LVF 2 creates a pixel-wide line on the detector array 3.

For a gap of 150 um, every "line" of light emerging from the LVF diverges at ±9.59°, creating a line ±25 um wide at the detector plane. This corresponds to the pixel pitch (50 um). Thus the wavelength-sensitive response of every line on the LVF 2 is split in a weighted fraction between two pixels. Accordingly, a gap less than 500 um, preferably less than 200 um, and more preferably between 5 um and 80 um, is preferred to minimize the optics required enabling the device to be provided in a small package.

Figures 13A, 13B:
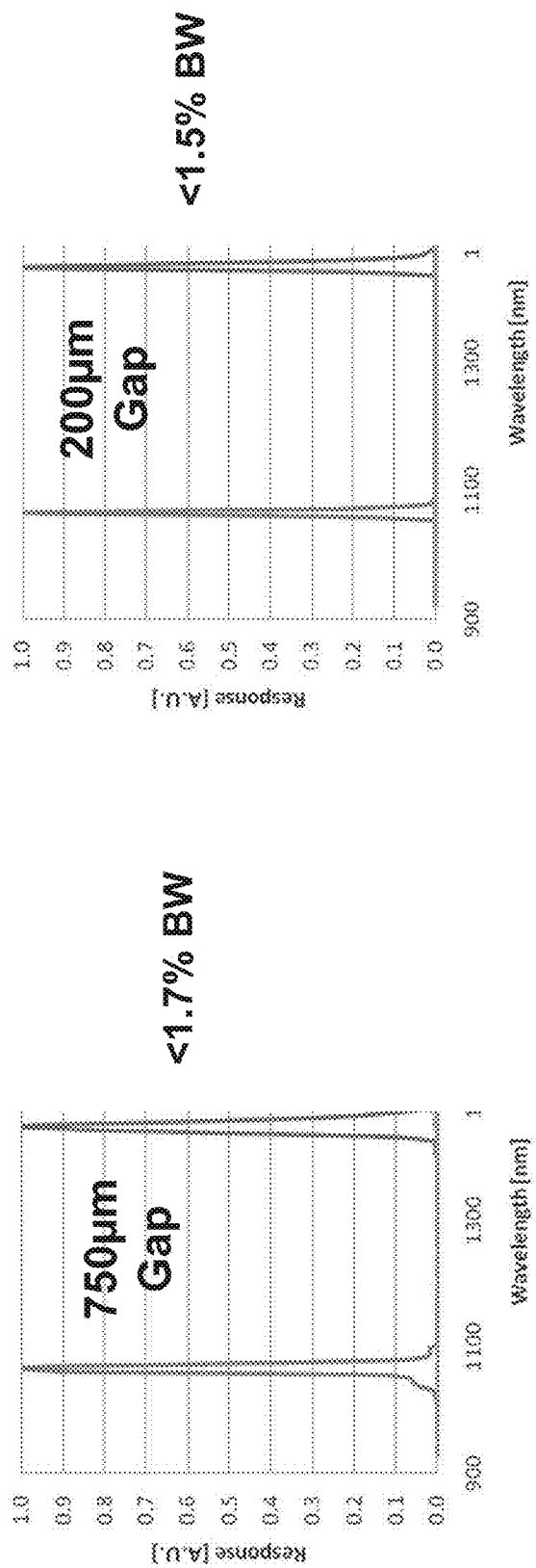
FIGS. 13a and 13b are plots of response vs wavelength for a spectrometer with a 750 um gap and with a 200 um gap, respectively, between LVF and detector array of the present invention

FIGS. 13a and 13b illustrate the difference in spectral performance for a gap of 750 um (FIG. 10a) and 200 um (FIG. 10b), wherein the smaller 200 um gap minimizes pixel cross talk, spectral broadening, and pedestals.

Ideally, the LVF 2 is as close to the detector array 3 as possible to mitigate spectral cross-talk between detector elements, as illustrated in FIG. 14. The best condition would be to directly attach the LVF 2 to the pixels 52 of the detector array 3 using an optically transmissive adhesive 51; however, the adhesive 51 also needs to: be electrically non-conductive or dielectric in nature; be mechanically neutral by achieving good adhesion strength with inducing stress or destructive forces to the detector array 3; optically compatible to transmit the desired spectral content; remove reflection created at air to glass interfaces; and have reasonable coefficient of thermal expansion properties to minimize stress to the detector pixels 52 during curing and during thermal cycling. Accordingly, then the LVF 2 makes each pixel 52 of the detector array 3 ideally respond to a different wavelength.

For example, the internal electronic components and wires 53 of the detector array 3, e.g. an InGaAs linear diode array, are very sensitive to any electrically conducting material, which will short out, damage or destroy the detectors pixels or CMOS processing chip 54. An adhesive material 51 that mitigates this problem in this example is Epo-Tek 353ND™, which is thermally curable not UV curable in nature. In this case thermally curable is acceptable, because the coating on the LVF 2, being directly attached to the pixels 52 on the detector array 3, will not transmit UV energy. Moreover, EP 353ND (Clear or Black) has excellent dielectric properties before and after the curing process. Ideally, EP 353ND Clear can be used as the adhesive 51 between the LVF 2 and the detector array 3 at a thickness of about 5 to 15 microns.

A "glass cover" 55, i.e. the substrate of the LVF 2 is provided over the LVF 2 covering most of the pixels 52 in the detector array 3, but not over the environmentally sensitive parts 53 of the sensor-bearing chip 54. However, the adhesive EP 353ND also comes in an opaque, e.g. black, form that could be used as a potting agent 56 for the entire internal package. The opaque adhesive 56 would serve as an optical isolator or light absorbing encapsulant or baffle, surrounding the LVF 2 and covering the sensitive electrical components of the detector array 3, within the package to minimize stray light problems. The adhesive potting agent 56 would also serve as an environmental protectant for the electronics 53 within the package without the need of a cover window as currently required. Using the same material as the clear adhesive 51 and the black potting material 56 has advantages thermally, optically and in manufacturing.

Thus, there are three factors that affect the resolution (range of wavelengths) that each pixel sees: first, the pixel width corresponds geometrically to a range of center wavelengths on the LVF 2, for example, a 50 um pixel with an LVF that ranges from 900-1700 nm sees 6.3 nm of wavelength. Second, the LVF 2 has an innate bandwidth set by the combination of design and cone angle of incident light (for example, 1% wide, or 9 nm to 17 nm, depending upon location). Third, the gap and cone angle impose a blurring or weighting effect (for example, 1 pixel wide, or an additional 6.3 nm, as a weighted average). It is the superposition of these that sets the overall resolution of the instrument, e.g. in our current instrument, 1.1%.

Possible applications for the portable spectrometer 1 include in-the-field threat detection; identification and validation of pharmaceuticals, controlled substances, and food products; forensics; process monitoring in the food industry (for example, moisture content in grains); and identification of products for recycling and contamination detection. Whatever has a near IR signal (structure) can be measured and determined.

In an alternate embodiment, illustrated in FIG. 15, the handheld compact spectrometer 1 includes the optical package coupled to a battery-pack 59 and a Bluetooth or WiFi chip 60 for communicating with the controlling device 7, e.g. control hardware and software, provided at remote locations.

A user will be using the compact spectrometer 1 connected to an Android, Windows-based, or Apple iOS-based device, i.e. the controlling device 7, for real-time predictions. Ideally, the controlling device 7 and the compact spectrometer 1 communicate via the USB cable 6 or a standalone Bluetooth or WiFi connection, i.e., they are the only two devices on this local network. There is no cloud interface; the user would upload a method file 62 or an app with a hardcoded method to non-transitory memory of the controlling device 7, and the controlling device 7 is expected to control the compact spectrometer 1 and execute the stored method file 62. The method file 62 refers to the combination of pre-processing and spectral model(s) derived from a spectral library, which delivers a prediction to the end user of the compact spectrometer 1. The method file 62 may contain more than one model if multiple results are desired for the application. The method file 62 may also prescribe the desired compact spectrometer configuration, e.g. exposure time, number of scans to average, or leave these settings to be defined as part of the instrument setup procedure.

Pre-processing are techniques of mathematical data treatment, or processing, to remove various effects in a set of the measured spectra, such as baseline offset or sample light scattering. Techniques include derivatives, scatter and baseline corrections. The specific choice of pre-processing is chosen to enhance discrimination, i.e. to minimize the difference between multiple spectra of the same material and maximize the difference between spectra of dissimilar materials.

A spectral library is a series of spectral measurements of known "reference" materials, either a variety of different substances or multiple versions of a single material type stored in non-transitory memory on the controlling device 7 or a server 64 connected thereto. Examples might be a series of near infrared (NIR), infrared (IR) or Raman spectra of different samples of white powders. The spectral library will be used to generate a 'spectral model'.

A 'spectral model' refers to a mathematical equation derived from a specific set of spectra. Models are typically regression vectors, derived statistically from the spectral library, which quantify the similarity of an unknown spectrum to those in the library. For example, a "spectral model" can include wavelengths, amplitudes, and widths of spectral peaks corresponding to a given material. These wavelengths, amplitudes, and widths are compared to the wavelengths, amplitudes, and widths of measured pre-processed spectra. The results of this comparison may be interpreted by a prediction engine 63 either qualitatively, for ID or pass/fail applications, or quantitatively, for determination of purity or concentration.

The prediction engine is comprised of computer hardware and/or software stored in non-transitory memory on the controlling device 7. The determined parameter or result is referred to as 'prediction'. The prediction provided by the prediction engine 63 can be transmitted to the compact spectrometer 1 for the user to observe or simply observed on suitable graphic user interface on the controlling device 7. Alternatively, the prediction can be stored in non-transitory memory on the controlling device 7 or the remote server 64 for future review.

The prediction engine 63 may make predictions in one of two ways; first, simple methods using known models and pre-processing may be performed directly in the spectrometer provider software. Second, complex or third-party-proprietary methods may be uploaded in a third-party format, and the controlling device 7 would communicate with a third-party prediction "engine" to perform real-time predictions. The third-party engine would need to be resident on the controlling device 7. Data reduction or projection techniques can include Partial Least Squares, Principle Component Analysis, Principle Component Regression, Partial Least Square Discriminate Analysis, and Soft Independent Modeling of Class Analogy.

Some users may wish to preserve a history of scans and predictions. For this purpose, the controlling device 7 will have the ability to save spectra and predictions locally and synchronize to a server 64 upon connection to the network (for example, via USB, WiFi, Bluetooth or 4G network). The controlling device 7 will also have the ability to receive updated methods from the server 64 when synchronizing. Bar-code reader for appropriate method selection may be desired in this scenario.

The method software 62 will have the ability to transmit unknown spectra via the server 64 to engineering for further evaluation or calibration update.

In addition to storing and executing methods, the application method 62 on the controlling device 7 will be able to set up and check the health of the spectrometer 1, for example, perform reference measurements. The 'diagnostic' capability of the compact spectrometer 1 will include measurement of an external wavelength accuracy standard (NIST 2036 or equivalent) and verification that the instrument accuracy is intact. Photometric noise and linearity calculations are also required. The diagnostic scans can be done during initial start-up or upon user request.

Figure 16:
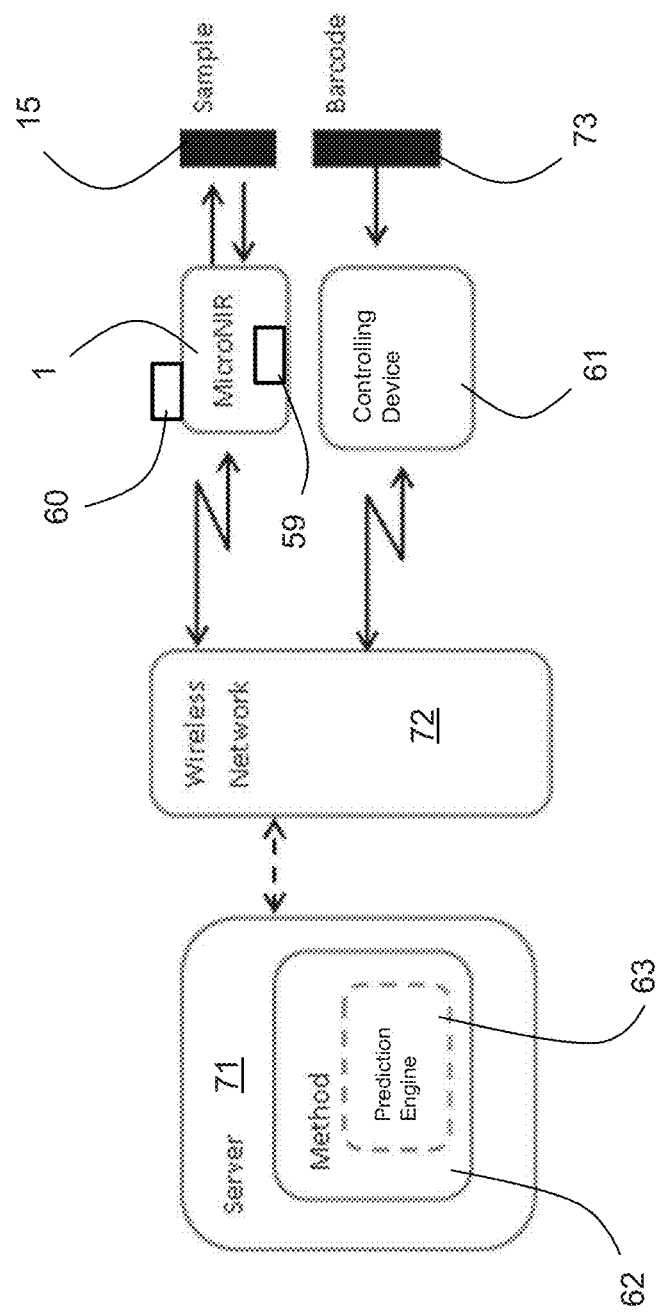
FIG. 16 is a schematic illustration of an alternative wireless spectrometer system in accordance with the present invention.

In an alternate configuration, illustrated in FIG. 16, the compact spectrometer 1 and the controlling device 7 are connected to each other and to a user's server 71 via a wireless network 72. An example of such a system being a receiving dock at a pharmaceutical company. The method file 62 and the prediction engine 63 are stored on the server 71 instead of the controlling device 7. In the infrastructure mode, the user will be able (or even required) to scan a barcode 73 of the sample 15 to be analyzed. The software stored in non-transitory memory and executed on the controlling device 7 will use barcode recognition algorithms on a photo taken with a camera on the controlling device 7, and use the barcode 73 to select an appropriate method from the server 71, and label the recorded spectrum and result appropriately for display and storage. The user will then scan the material by pressing the integrated scan button of the compact spectrometer 1. The user may also want to command the scan from the controlling device 7. When the scan is complete, the user will view the predicted result on the controlling device 7 and acknowledge the result based upon the method. If bar code integration is not in effect at the user site, the user shall be able to select the appropriate method file from a list stored on the server 71 before performing the spectral acquisition with the compact spectrometer 1.

In a special case within infrastructure mode, the operator may configure the compact spectrometer 1, including selecting a method, and then carry just the spectrometer 1 to scan samples in a single pass/fail evaluation. In this mode, the spectrometer 1 will communicate with the controlling device 7 and via the WAN 72, be triggered by the integrated scan button, and provide audible, visual or tactile (vibratory) feedback as to pass/fail results.

The methods, spectra and results will all be saved/stored on the user database server 71, not on the controlling device 7. Additionally, methods may be executed on the local cloud, i.e. the server 71, with the result passed back to the controlling device 7, which are transparent to the user. A user with appropriate privileges should have the ability to view results from multiple compact spectrometers 1 and offer privilege management for multiple users, e.g. the ability to generate or only use methods, by interacting with the local cloud. 21 CFR Part 11 compliant software is required for this scenario, as such; each user shall have different 'administrative' privileges allowing trained operators to only use the compact spectrometer 1 as they are allowed. 21 CFR Part 11 also provides a mechanism for data authenticity, where no data can be deleted or altered without appropriate authority. The local server 71 is expected to be an integral part of 21CFR Part 11 compliance.

In yet another configuration, which is highly specific to the application of the compact spectrometer 1, the core architecture of cloud-based computing is critical. The core architecture and the measurement process is similar to that depicted in FIG. 17.

The user for this configuration is a novice and does not necessarily have experience with NIR technology or the spectrometer 1. The user is merely looking for the spectrometer 1 to provide an answer based on a very specific sampling and testing procedure. The typical jargon is "standard operating procedure," or SOP. A law enforcement officer, a hazmat technician, or military personnel are good examples.

A sophisticated app on the controlling device 7 will guide the user through initialization and configuration of the compact spectrometer 1. The app will download updates and methods, as needed, from the spectrometer provider's server 71 disposed in a remote and secure location, e.g. via one or more networks, such as the internet, and report diagnostics back to the spectrometer provider's server 71. In this configuration, the option of fully characterizing and periodically verifying the instrument to the point that baseline and zero would no longer have to be performed in the field and setup would be completely automatic, is provided.

In "Cloud-Based Operation mode", the spectrometer provider's personnel will be responsible for managing method software 62 and monitoring system health and performance. The method software 62 will be owned and managed by the provider of the spectrometer 1. As such, any updates to the method software 62 will need to be 'pushed' to the local subscriber base.

Similarly, results and data generated by the spectrometer 1 will be relayed back to the server 71 of the spectrometer provider (or their partner), and archived for possible future use. The data coming back to the spectrometer provider server 71 from the end user's samples 15 will be screened for statistical similarity or uniqueness based upon both the results from the field and upon further analysis of uploaded spectra by methods applied at the spectrometer provider server 71. If the sample is deemed unique when compared to the spectrometer provider's library, the spectrum will be flagged as a possible addition to the future method update (and the user will be notified and requested to provide more information). In essence, this is collecting unique samples for future inclusion to the model to account for any variability not currently addressed by the existing method.

We claim:

1. A portable spectrometer device comprising:
an illumination source for directing light at a sample;
a tapered light pipe (TLP) for capturing light interacted with the sample at a first focal ratio and for delivering the light at a second focal ratio lower than the first focal ratio;
a linearly variable filter (LVF) for separating the captured light into a spectrum of constituent wavelength signals; and
a detector array, including a plurality of pixels, each of the plurality of pixels disposed to receive at least a portion of one of the constituent wavelength signals providing a power reading for each constituent wavelength;
wherein the TLP includes a first smaller end for positioning adjacent to the sample, a second wider and taller end adjacent to the LVF, and sidewalls diverging from the first end to the second end for mixing and spreading the light across the LVF;
wherein the LVF and the detector array are separated by a gap of less than 200 um, for increasing spectral resolution;
wherein the LVF is bonded directly to the detector array; and
wherein the gap comprises an optically transparent adhesive 5 to 15 microns thick.

2. The device according to claim 1, further comprising a housing; and a control system within the housing, the control system comprised of a processor, a suitable non-transitory memory, and a USB connector for receiving a USB cord, enabling transfer of data between the processor and a host computer.

3. The device according to claim 1, further comprising a Bluetooth or WIFI chip for communicating with a controlling device, which sends tests procedures and receives test results.

4. The device according to claim 1, further comprising a battery or a USB cable connector for providing the spectrometer device with less than 2.5 W of power.

5. The device according to claim 1, further comprising a housing for enclosing the illumination source, the TLP, the LVF and the detector array, wherein the housing is less than 2"×2".

6. The device according to claim 5, wherein the housing, the illumination source, the TLP, the LVF and the detector array weigh less than 0.5 pounds.

7. The device according to claim 1, wherein the illumination source comprises at least one light source, disposed at an acute angle from a longitudinal axis of the LVF, for generating a spot on the sample, whereby light is reflected from the sample along the longitudinal axis into the LVF.

8. The device according to claim 7, wherein each light source comprises a lens tipped vacuum tungsten lamp for creating a less than 5 mm spot on the sample.

9. The device according to claim 7, wherein the illumination source comprises two light sources; and wherein an end of the TLP is disposed between the two light sources.

10. The device according to claim 1, wherein the gap ensures that a single line on the LVF creates a pixel-wide line on the detector array.

11. A portable spectrometer device comprising:
an illumination source for directing light at a sample;
a tapered light pipe (TLP) for capturing light interacted with the sample at a first focal ratio and for delivering the light at a second focal ratio lower than the first focal ratio;
a linearly variable filter (LVF) for separating the captured light into a spectrum of constituent wavelength signals; and a detector array, including a plurality of pixels, each of the plurality of pixels disposed to receive at least a portion of one of the constituent wavelength signals providing a power reading for each constituent wavelength;

wherein the TLP includes a first smaller end for positioning adjacent to the sample, a second wider and taller end adjacent to the LVF, and sidewalls diverging from the first end to the second end for mixing and spreading the light across the LVF;

wherein the TLP accepts light at the first focal ratio of f/1 with a cone angle of between 20° and 40°, and delivers a reflected light to the LVF with second focal ratio of less than f/3 with a cone angle of less than 10°.

12. The device according to claim 11, wherein the TLP includes a lensed exit face for straightening tilted ray bundles for delivery to the LVF.

13. The device according to claim 11, wherein the LVF and the detector array are separated by a gap of less than 200 um, for increasing spectral resolution.

14. The device according to claim 13, wherein the gap ensures that a single line on the LVF creates a pixel-wide line on the detector array.

15. The device according to claim 13, wherein the LVF is bonded directly to the detector array; and wherein the gap comprises an optically transparent adhesive 5 to 15 microns thick.

16. A portable spectrometer device comprising:
an illumination source for directing light at a sample;
a tapered light pipe (TLP) for capturing light interacted with the sample at a first focal ratio and for delivering the light at a second focal ratio lower than the first focal ratio;
a linearly variable filter (LVF) for separating the captured light into a spectrum of constituent wavelength signals;
a detector array, including a plurality of pixels, each of the plurality of pixels disposed to receive at least a portion of one of the constituent wavelength signals providing a power reading for each constituent wavelength; and
a TLP boot including a support section for supporting the TLP, and a spacer section for spacing the TLP from the sample ensuring that the light from the sample is presented to the TLP at a desired acceptance angle defined by the first focal ratio f/1 with a cone angle of about 30°,
wherein the TLP includes a first smaller end for positioning adjacent to the sample, a second wider and taller end adjacent to the LVF, and sidewalls diverging from the first end to the second end for mixing and spreading the light across the LVF.

17. The device according to claim 16, wherein the spacer section of the TLP boot includes stepped inner walls for reducing specular reflections from reaching the TLP.

18. The device according to claim 16, wherein the LVF is bonded directly to the detector array forming a gap therebetween; and wherein the gap comprises an optically transparent adhesive 5 to 15 microns thick.

19. A portable spectrometer device comprising:
an illumination source for directing light at a sample;
a tapered light pipe (TLP) for capturing light interacted with the sample at a first focal ratio and for delivering the light at a second focal ratio lower than the first focal ratio;
a linearly variable filter (LVF) for separating the captured light into a spectrum of constituent wavelength signals;
a detector array, including a plurality of pixels, each of the plurality of pixels disposed to receive at least a portion of one of the constituent wavelength signals providing a power reading for each constituent wavelength; and
a temperature feedback system for adjusting the power reading of each constituent wavelength based on an ambient temperature;
wherein the TLP includes a first smaller end for positioning adjacent to the sample, a second wider and taller end adjacent to the LVF, and sidewalls diverging from the first end to the second end for mixing and spreading the light across the LVF.

20. A spectrometer system comprising:
a portable spectrometer device comprising:
an illumination source for directing light at a sample;
a tapered light pipe (TLP) for capturing light interacted with the sample at a first focal ratio and for delivering the light at a second focal ratio lower than the first focal ratio;
a linearly variable filter (LVF) for separating the captured light into a spectrum of constituent wavelength signals; and
a detector array, including a plurality of pixels, each of the plurality of pixels disposed to receive at least a portion of one of the constituent wavelength signals providing a power reading for each constituent wavelength;
wherein the TLP includes a first smaller end for positioning adjacent to the sample, a second wider and taller end adjacent to the LVF, and sidewalls diverging from the first end to the second end for mixing and spreading the light across the LVF;
a controlling device operably coupled to the portable spectrometer device for controlling the portable spectrometer device; and
a server operably coupled to the portable spectrometer device and the controlling device via a wireless digital network for storing spectrums;
wherein the server is configured to receive the spectrum from the portable spectrometer device; to compare the spectrum to a library of spectrum models; and to output a result of the comparison to a display;
wherein the server includes a store of scan characteristics and spectrum models; and
wherein the controlling device includes a barcode reader, wherein in operation, the barcode reader reads a barcode corresponding to the sample, the controlling device communicates the barcode to the server, and the server selects the scan characteristics and spectrum models for comparison based on the barcode.

21. The system according to claim 20, wherein the controlling device is configured to receive the spectrum from the portable spectrometer device; to compare the spectrum to a library of spectrums; and to output a result of the comparison to a display.

* * * * *

UNITED STATES PATENT AND TRADEMARK OFFICE
CERTIFICATE OF CORRECTION

PATENT NO. : 9,234,839 B2
APPLICATION NO. : 14/079280
DATED : January 12, 2016
INVENTOR(S) : Curtis R. Hruska et al.

Page 1 of 1

It is certified that error appears in the above-identified patent and that said Letters Patent is hereby corrected as shown below:

Title Page

Please correct the Inventors (72) to read as follows:

Curtis R. Hruska, Cloverdale, CA (US);
Charles A. Hulse, Sebastopol, CA (US);
Brett J. Bryars, San Carlos, CA (US);
Marc K. Von Gunten, Novato, CA (US);
Christopher G. Pederson, Santa Rosa, CA (US);
Nada A. O'Brien, Santa Rosa, CA (US)
Jerry Zieba, Santa Rose, CA (US)
Benjamin F. Catching, Santa Rosa, CA (US)

Signed and Sealed this
Second Day of August, 2016

Michelle K. Lee
*Director of the United States Patent and Trademark Office*